(12) United States Patent
Tjin (10) Patent No.: US 6,325,762 B1
(45) Date of Patent: Dec. 4, 2001

(54) METHOD AND APPARATUS FOR CONTINUOUS CARDIAC OUTPUT MONITORING

(76) Inventor: Swee Chuan Tjin, Block 835 83 Woodlands Street #08-129, Singapore 730853 (SG)

(*) Notice: Subject to any disclaimer, the term of this patent is extended or adjusted under 35 U.S.C. 154(b) by 0 days.

(21) Appl. No.: 09/319,708

(22) PCT Filed: Dec. 4, 1997

(86) PCT No.: PCT/SG97/00066

§ 371 Date: Aug. 23, 1999

§ 102(e) Date: Aug. 23, 1999

(87) PCT Pub. No.: WO98/25513

PCT Pub. Date: Jun. 18, 1998

(30) Foreign Application Priority Data

Dec. 9, 1996 (SG) ................................ 9611605-8

(51) Int. Cl.⁷ .............................. A61B 5/02; G02B 6/06; G01N 15/02
(52) U.S. Cl. ...................... 600/505; 600/504; 600/342; 356/336; 385/119
(58) Field of Search ................... 600/505, 504, 600/488, 486, 485, 561, 342; 606/15, 16; 356/336, 338, 342; 385/116, 117, 119

(56) References Cited

U.S. PATENT DOCUMENTS

| 4,281,929 | * | 8/1981 | Lord et al. ........................ 356/241.1 |
| 4,529,267 | * | 7/1985 | Nishioka et al. ..................... 385/117 |
| 4,691,709 | * | 9/1987 | Cohen ................................. 600/138 |
| 4,721,115 | | 1/1988 | Owens . |
| 4,873,989 | * | 10/1989 | Einzig ................................. 600/505 |
| 4,913,142 | | 4/1990 | Kittrell et al. . |
| 5,058,583 | | 10/1991 | Geddes et al. . |
| 5,092,339 | | 3/1992 | Geddes et al. . |
| 5,178,153 | * | 1/1993 | Einzig ................................. 600/505 |
| 5,509,424 | * | 4/1996 | Al-Ali ................................. 600/505 |
| 5,512,034 | * | 4/1996 | Finn et al. ........................... 600/138 |
| 5,682,899 | * | 11/1997 | Nashef et al. ...................... 600/505 |
| 6,166,806 | * | 12/2000 | Tjin .................................... 356/336 |

FOREIGN PATENT DOCUMENTS

| G 87 14 775 U | 2/1988 | (DE) . |
| 37 35 190 C1 | 5/1989 | (DE) . |
| 40 04 736 A1 | 8/1991 | (DE) . |
| 0 392 897 | 10/1990 | (EP) . |
| 0 455 334 A1 | 11/1991 | (EP) . |
| 2 198 840 A | 6/1988 | (GB) . |
| WO90/12537 | 11/1990 | (WO) . |
| WO94/22367 | 10/1994 | (WO) . |
| WO97/12210 | 4/1997 | (WO) . |

* cited by examiner

*Primary Examiner*—John P. Lacyk
*Assistant Examiner*—Navin Natnithithadha
(74) *Attorney, Agent, or Firm*—Pillsbury Winthrop LLP (57) ABSTRACT

An apparatus for continuous cardiac output monitoring ascertains cardiac output by measuring the cross-sectional area of the vessel and the flow rate of fluid flowing through the vessel. The cross-sectional area is derived from the measured resistance within the vessel whereby a pair of signal electrodes injects a known electrical signal into the vessel and the resistance is derived from the known signal and the differential voltage between first and second measuring pairs of electrodes. Resistivity of the fluid is a component of the cross-sectional area derivation, and a temperature sensor is provided to allow for compensating for variations in resistivity with temperature. A velocity sensor is preferably of an optic fiber, Doppler shift type, and the accuracy of the velocity measurement is improved by focusing light emissions from the optic fiber(s) by either providing a Fresnel plate on the terminal end of the fiber or by forming the terminal end of the fiber in a generally conical shape.

13 Claims, 7 Drawing Sheets

METHOD AND APPARATUS FOR CONTINUOUS CARDIAC OUTPUT MONITORING

BACKGROUND OF THE INVENTION

1. Field of the Invention

The present invention relates to a method and apparatus for continuously monitoring cardiac output in which accuracy is improved by improving the accuracies of the measurements of the components of the cardiac output derivation.

2. Description of the Prior Art

The heart is a major organ of a person. This pumping station circulates blood through the entire body sending critical nutrients and oxygen to maintain the body's metabolic demands. A measure of the heart's performance is therefore very important to physicians. One very useful parameter is the cardiac output (CO).

Cardiac output is the volume of blood pumped out of the heart through the aorta to the rest of the body in one minute. A "typical" 68.7 kg person with a total blood volume of 5200 ml has a CO of 5345 ml/min at a heart rate of 80 beats/min. This works out to be 67.2 ml/beat.

At present several techniques are used to measure CO. There exist both direct and indirect methods. Direct methods of monitoring CO include the Indicator-Dilution method. The Indicator Dilution method covers a range of techniques such as: thermodilution, Fick and dye dilution. These techniques generally employ the introduction of a detectable indicator into a vessel upstream and measuring the indicator concentration (time curve) downstream. The thermodilution method is used as the standard in clinical medicine for measuring CO. However, these methods are cumbersome and are only able to give average CO values. Furthermore, continuous monitoring of CO using these methods is not possible as the indicator cannot be indefinitely introduced into the patient. There is a need for on-line continuous monitoring of CO for cardiac pacing and bedside monitoring. The indirect methods employ ultrasound and electromagnetic techniques. These methods are able to provide instantaneous single stroke information. However, they are only able to give flow velocity and not volumetric flow.

Kubicek et al. introduced another non-invasive impedance technique for obtaining continuous CO in their article "Development and Evaluation of an Impedance Cardiac Output System", Aerospace Med., 37, p. 1208, 1966. This thoracic impedance method involved the use of four electrodes placed transversely around a person, two around the neck and two around the thorax. The system has two outer current injecting electrodes and two inner potential electrodes. However, the method does not yield good estimates of CO in sick patients. Nevertheless, the impedance technique provides a means of obtaining on-line continuous CO.

Another technique involving impedance measurements for the determination of CO is the measurement of ventricular volume by means of an intracardiac conductance catheter as disclosed Dimensions Obtained With Impedance Catheter," Cardiovase Res., Vol. 15, pp, 328–34, 1991. This technique measures the changing ventricular volume which is the stroke volume (CO is the total stroke volume of the heart in one minute). This method did look promising. However, it was found that the conductance is not a linear function of the volume. This could be due to the ventricle's highly irregular shape and this shape varies over the cardiac cycle.

Figure 13:
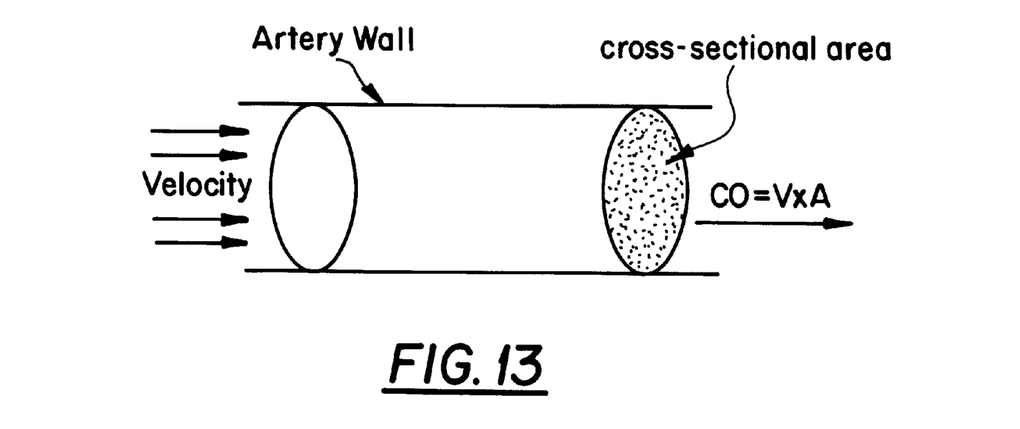
FIG. 13 is a schematic view of an artery illustrating the analytical components for calculating cardiac output.

An alternative method was proposed for a continuous cardiac output monitoring system. This method calculates CO by taking the product of the velocity of blood flow and the cross-sectional area of the artery (likely the aorta) as illustrated in FIG. 13.

A dual fiber laser doppler anemometer developed by Tjin for accurate in vivo blood low measurements can be used to measure the velocity of blood flow while the cross-sectional area of the artery can be determined by an electrical impedance method. This impedance technique is based on the relationship:

$$R = \frac{\rho l}{A}$$

where,

R is Resistance (Impedance);

$\rho$ is the resistivity of the medium;

l is the separation of the measuring electrodes; and

A is the cross-sectional area.

In this relationship, it is assumed that the electric field generated by the electrodes is uniform.

In 1995, Chew, H. L., et al. measured the impedance of blood using two electrodes and disclosed their method and results in "Continuous Cardiac Output Monitoring by Impedance Measurements in the Artery," FYP Report, Nanyang Technological University, p. 12, 1995. However, in a two electrode system, the electric field generated is non-uniform, which deviates from the assumption of a uniform field between the two electrodes in the above equation. This non-uniform field produces a non-linear relationship between area and resistance.

With a four-electrode probe, where the current is injected by two outer field electrodes and the potential is measured by two inner measuring electrodes, polarization problems in a non-uniform electric field are minimized.

A four-electrode system does, however, suffer from inaccuracies due to the fact that a layer of electric charge will build up at the electrode electrolyte interface. Accordingly, the measured impedance will be too high due to the extraneous charge which gives rise to additional impedance between the two measuring electrodes.

In addition, it has been found that the resistivity $\rho$ of the medium, typically blood, changes with temperature by about 2.4% per degree celsius temperature change. Accordingly, the cross-sectional area derived from the resistivity of the medium can vary with temperature in a manner which affects the indicated CO.

SUMMARY OF THE INVENTION

It is an object, therefore, of this invention to provide a method and apparatus for continuously monitoring cardiac output in a manner which avoids the inaccuracies and disadvantages of the prior art methods and apparatuses. Accuracy of cardiac output measurements can be improved by improving the accuracy of either or both of the measurements which constitute the components of the cardiac output derivation. Specifically, accuracy can be enhanced by improving the accuracy of the measurement of the flow velocity and/or of the cross-sectional area. Accordingly, consistent with the object of providing improved continuous cardiac output monitoring, the present invention provides for improved accuracies in the measurements of the flow velocity and of the cross-sectional area.

The cross-sectional area is directly proportional to the resistivity, $\rho$, of the fluid and is inversely proportional to the electrical resistance, or impedance, within the vessel.

Thus, the accuracy of the cross-sectional area derivation can be improved by compensating for temperature variations in the resistivity of the medium flowing in the vessel. Such improved cross-sectional area derivation, and thereby improved continuous cardiac output monitoring, is achieved by an apparatus for continuously monitoring the volume flow rate of a fluid flowing through a vessel based on the relationship, Q=V×A, where Q is the volume flow rate, V is the velocity of the fluid flowing through the vessel, and A is the cross sectional area of the vessel proximate a location in the vessel where the flow velocity is measured.

The apparatus comprises a cross-sectional area sensor for deriving the cross-sectional area of the vessel based on an electrical impedance within the vessel. The cross-sectional area sensor comprises an impedance measuring instrument constructed and arranged to continuously ascertain the electrical impedance of the vessel, and the derived cross-sectional area is directly proportional to the resistivity, $\rho$, of the fluid flowing in the vessel and inversely proportional to the resistance, R, of the vessel.

The apparatus further includes a velocity sensor for measuring the velocity of the fluid flowing in the vessel and a temperature sensor for continuously measuring the temperature of the fluid flowing in the vessel so as to allow continuous compensation in the cross-sectional area derivation for variations in the resistivity $\rho$ with temperature.

Moreover, improved cardiac output monitoring is achieved through a method for continuously monitoring the volume flow rate of a fluid flowing through a vessel based on the relationship, Q=V×A, where Q is the volume flow rate, V is the velocity of the fluid flowing through the vessel, and A is the cross sectional area of the vessel proximate a location in the vessel where the flow velocity is measured. The method comprises the steps of ascertaining the electrical impedance of the vessel and deriving the cross-sectional area of the vessel based on the electrical impedance within the vessel, wherein the derived cross-sectional area is directly proportional to the resistivity, $\rho$, of the fluid flowing in the vessel and inversely proportional to the resistance, R, of the vessel. The method further includes the steps of measuring the velocity of the fluid flowing in the vessel and measuring the temperature of the fluid flowing in the vessel and compensating in the cross-sectional area derivation for variations in the resistivity $\rho$ with temperature based upon the measured temperature.

The accuracy of the cross-sectional area derivation can also be improved by improving the accuracy of the impedance measurement. Such improved cross-sectional area derivation is achieved by an instrument for ascertaining the impedance of a vessel in which the instrument is disposed, the cross-sectional area of the vessel being derivable from the ascertained impedance. The instrument comprises a pair of signal-emitting electrodes for injecting a known electrical signal into the vessel in which the instrument is disposed. First and second pairs of measurement electrodes are provided across which voltages can be measured. The signal-emitting electrodes inject the known signal into the vessel and a first voltage is measured across the first pair of measurement electrodes and a second voltage is measured across the second pair of measurement electrodes. The impedance of the vessel, from which the cross-sectional area can be derived, is determined from the known signal and the difference between the first and second voltages. By using differential voltages instead of measured voltages to ascertain the impedance, inaccuracies due to erroneous electrical charge build-up at the measuring electrodes are avoided.

The velocity is preferably measured by a fiber optic Doppler shift technique. The technique is carried out by a velocity sensor for remote fluid flow measurements which comprises a flexible tube having an optical opening formed in a sidewall thereof. An optical fiber having a longitudinal fiber axis is disposed within the tube, and the fiber has a terminal end disposed within the tube near the optical surface is disposed within the tube adjacent the terminal end of the optical fiber. The reflective surface is oriented such that the light emitted from the terminal end of the optical fiber is reflected by the reflective surface in a direction having a component normal to the fiber axis through the optical opening into a measurement volume of the flow located outside and alongside the sensor.

The accuracy of the fiber optic, Doppler shift sensor can be improved by focusing the light emitted from the optic fiber before it is reflected into the measurement volume. The fiber can be focused to cause the light emitted from the fiber to be focused in front of the terminal end by providing a plurality of concentric Fresnel rings on an end face of the terminal end of the optical fiber or by forming the terminal end of the optical fiber in a generally conical shape.

Other objects, features and characteristics of the present invention will become apparent upon consideration of the following description with reference to the accompanying drawings, and in the appended claims, all of which form a part of the specification, and wherein reference numerals designate corresponding components of the figures.

DETAILED DESCRIPTION OF THE INVENTION

Figures 1, 2:
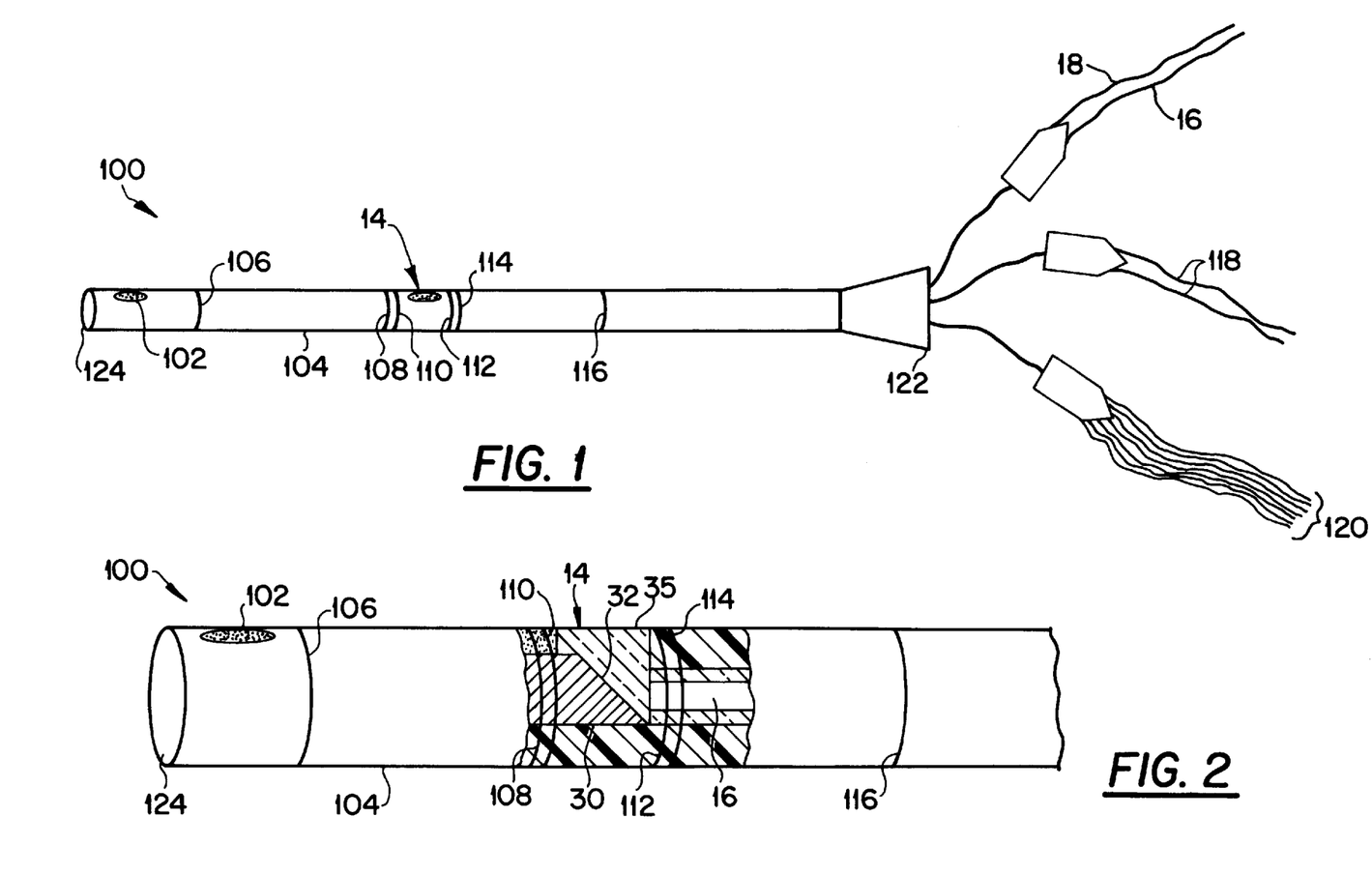
FIG. 1 is a partial perspective view of an apparatus for continuous cardiac output monitoring.
FIG. 2 is an enlarged partial view of the apparatus of FIG. 1.

An apparatus for monitoring cardiac output according to the present invention is generally designated by reference number 100 in FIGS. 1 and 2. In a catheter 104 having a proximal end 122 and distal end 124, the apparatus 100 is preferably provided in the catheter near the distal end 124.

The apparatus includes a cross-sectional area sensor, preferably comprised of six longitudinally spaced electrodes 106, 108, 110, 112, 114, and 116 extending circumferentially about catheter 104, a temperature sensor 102 preferably formed nearest to the distal end 124, and a velocity sensor 114 preferably centrally located amongst the electrodes 106, 108, 110, 112, 114, and 116. The various sensors are operatively connected to appropriate analyzing equipment (not shown). For example, temperature sensor 102 is connected by conductors 118, preferably copper wires. Velocity sensor 14 is preferably of a fiber optic, Doppler shift type and is preferably connected by two optic fibers 16, 18. Electrodes 106–116 are preferably connected by a plurality of conductors 120, preferably copper wires.

The catheter 104 in which the sensors are located is preferably a flexible tube made from a medical grade tubing, such as heparin (an anticoagulant) coated latex, which is conventionally used in a variety of in vivo applications.

The electrodes 106–116 of the cross-sectional area sensor may be steel wires having a width of 0.2 mm wrapped around the catheter 104. Conductive polymers may, however, prove to be a preferable material as they are less likely to corrode than steel. Moreover, although 0.2 mm wide electrodes have been used in experiments, a 0.2 mm width is not believed to be an optimum width.

In the present arrangement, the two outermost electrodes 106 and 116 are the signal electrodes, which are employed to inject a known signal into the medium as will be described below. The two innermost electrodes 110 and 112 constitute a first pair of measuring electrodes across which a first voltage is measured. Moving in from the outermost electrodes 106 and 116 or out from the innermost electrodes 110 and 112, the next electrodes 108 and 114 constitute a second pair of measuring electrodes across which a second voltage is measured.

The innermost electrodes 110 and 112, constituting the first measurement pair, are preferably spaced 5.5 mm apart. The intermediate electrodes 108 and 114, constituting the second measurement pair, are preferably each spaced at least 2 mm outside the innermost electrodes 110, 112.

Figure 12:
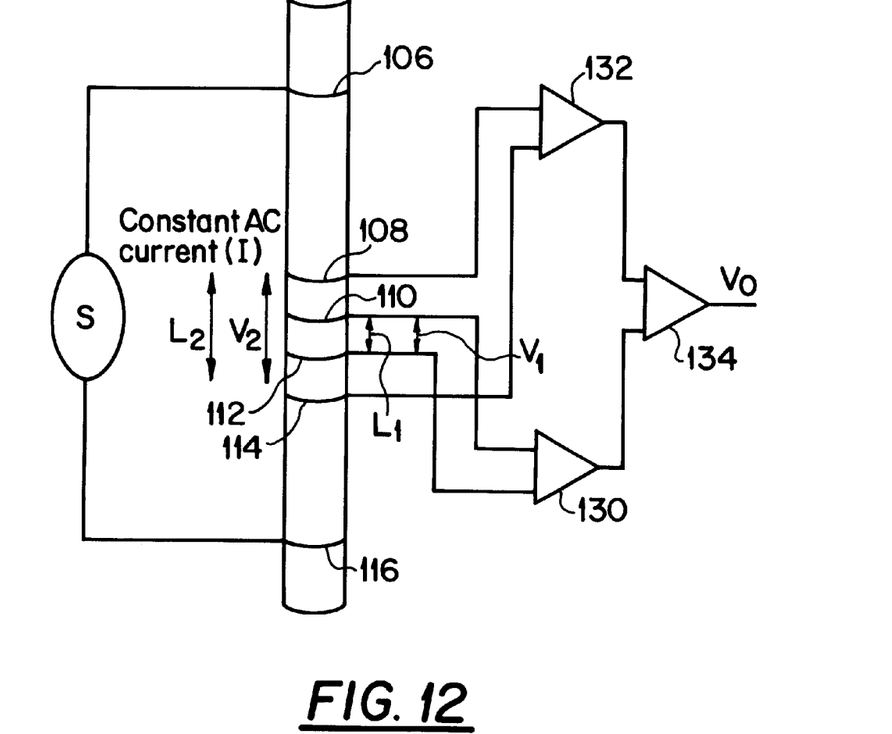
FIG. 12 is a schematic view of a cross sectional area sensor used in conjunction with the present invention.

The manner in which cross-sectional area is derived from the measurements at the electrodes will now be explained in conjunction with FIG. 12. As schematically shown in FIG. 12, a signal "S" with a constant AC current "I" is introduced into the medium via outside electrodes 106 and 116. Signal "S" is preferably a sine wave signal of frequency ranging from 1 KHz to 100 KHz.

Although the Association for the Advancement of Medical Instrumentation has set a standard that current through any measuring device to be used near the heart of a patient should not exceed 20 $\mu A$, it was found that current accidentally flowing into the patient's heart should not exceed 10 $\mu A$. Thus, it is preferred that "I" not exceed 10 $\mu A$.

As schematically shown in FIG. 12, a voltage "$V_1$" is measured across the first measurement pair of electrodes 110, 112. A voltage "$V_2$" is measured across the second measurement pair of electrodes 108, 114. $V_1$ is amplified in amplifier 130 and $V_2$ is amplified in amplifier 132. Amplifier 134 accepts the outputs of amplifiers 130 and 132 and outputs a voltage differential $V_0$.

Using the equation given above:

$$R = \frac{\rho l}{A}$$

the cross sectional area can be derived.

Let the interface impedance be $R_I$ then the resistances $R_1$ between the first pair of electrodes 110, 112 and $R_2$ between the second pair of electrodes 108, 112 are:

$$R_1 = \frac{\rho L_1}{A} + R_I; \quad R_2 = \frac{\rho L_2}{A} + R_I$$

Where $L_1$ and $L_2$ are the distances between the two sets of electrodes as depicted in FIG. 12.

Voltages corresponding to these resistances are:

$$V_1 = IR_1 = I\left(\frac{\rho L_1}{A} + R_I\right)$$

and $$V_2 = IR_2 = I\left(\frac{\rho L_2}{A} + R_I\right)$$

Where I is the current through the signal electrodes.

Taking a differential voltage between the two sets of electrodes yields:

$$V_1 - V_2 = \frac{\rho I(L_1 - L_2)}{A}$$

and thus;

$$A = \frac{\rho I(L_1 - L_2)}{V_1 - V_2}$$

For the amplifier, $V_0 = G(V_1 - V_2)$, where G is the gain of the amplifier. Hence the cross sectional area A is:

$$A = \frac{G\rho I(L_1 - L_2)}{V_o} = \frac{K}{V_o}$$

Where K is a constant. Thus the cross sectional area is inversely proportional to the output voltage of the amplifier.

As noted above in the "Background" section, the derived area can be erroneous because of impedance measurements which are too high due to the build-up of electric charge at the electrodeelectrolyte interface. These errors are eliminated in the present invention by using a voltage differential, instead of actual measured voltages.

The cross-sectional area derived from the resistivity of the medium can vary with temperature in a manner which affects the indicated CO. Using the linear relationship between area and temperature, which has been experimentally determined to be about 2.4% per degree celsius, temperature effects can be compensated for if the temperature is known.

Thus, temperature sensor 102 is provided. Temperature sensor 102 is preferably a thermistor wired into the diagnostic equipment to provide constant, real-time temperature compensation.

The velocity sensor will now be described.

The velocity sensor 14 is preferably a dual, fiber, fiber optic Doppler shift type sensor, although a single fiber sensor may be used, albeit with diminished accuracy. First and second optic fiber 16, 18 are preferably enclosed within flexible tube 104. The fibers are conventional optical fibers and can, for example, be comprised of glass or plastic. Glass fibers are preferred because of their superior light transmission qualities.

Velocity sensor 14 is located adjacent, but proximally of, a distal end 124 of the catheter 104, or at any desired location therealong. Conventional connectors are fixed to the proximal ends of the optic fibers 16, 18, respectively, to connect the fire fibers to an anemometer or other suitable analyzing device.

The constructions of various embodiments of the velocity sensor 14 are shown in more detail in FIGS. 3–11. For simplicity o f illustration, a velocity sensor used in conjunction with the present invention is shown in FIGS. 3–9 without a cross-sectional area sensor or a temperature sensor.

Figure 3:
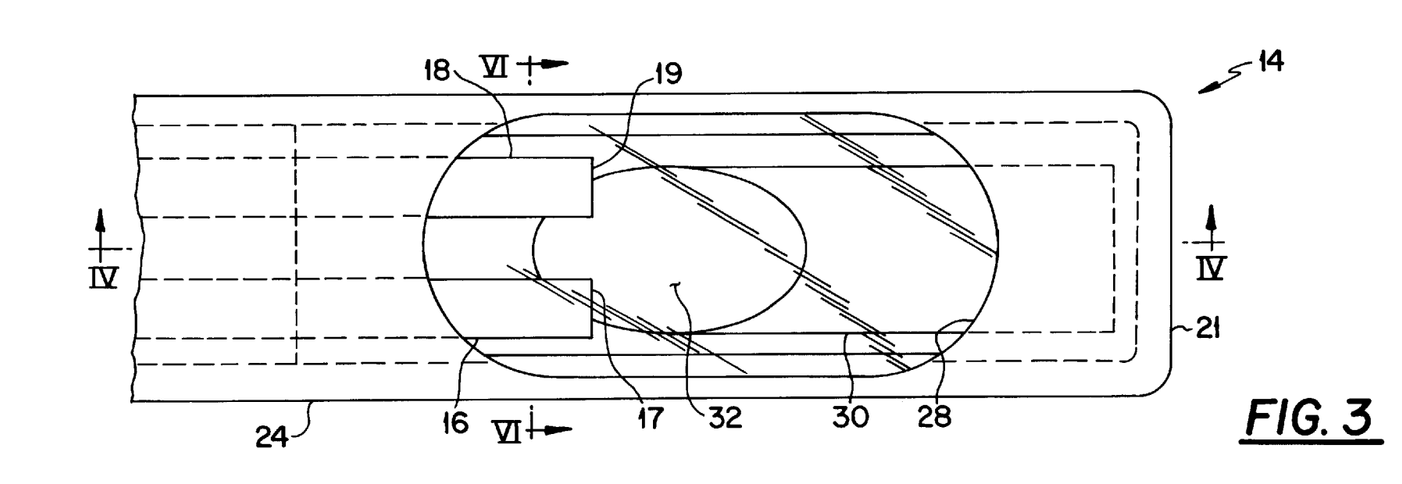
FIG. 3 is a partial plan view of a velocity sensor used in conjunction with the present invention, from above the reflective surface.
Figure 4:
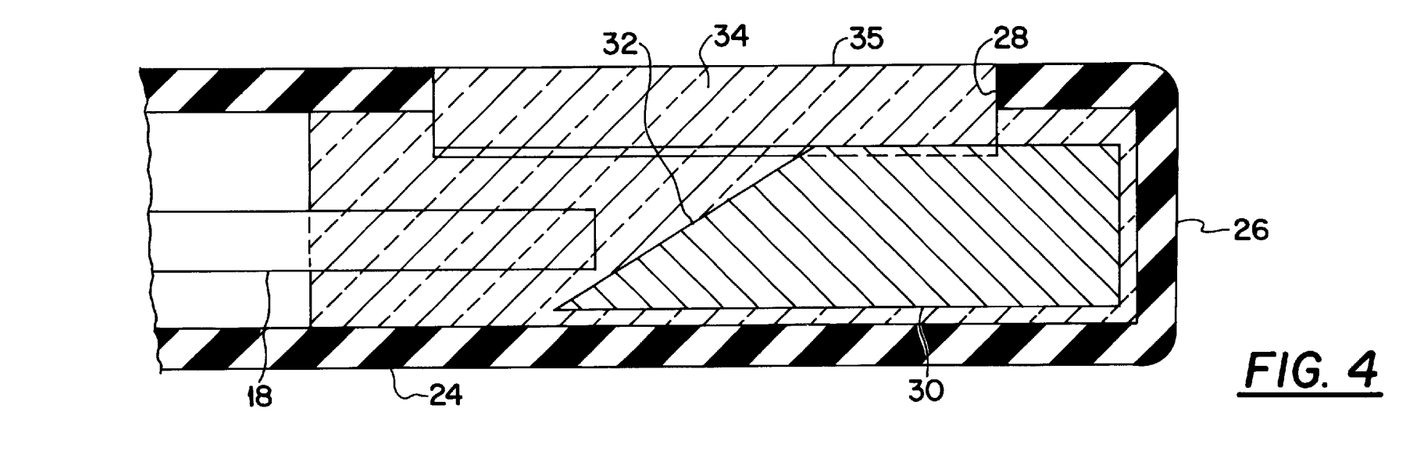
FIG. 4 is a cross-sectional view of the velocity sensor of FIG. 3 along the line "IV—IV"

Optic fibers 16, 18 are enclosed by the flexible tube 24 and may terminate within the tube 24 near, but spaced proximally from, the distal end 21 of the catheter. It is presently preferred to use multimode fibers having a step refractive index profile with a core diameter of 50 $\mu$m and a cladding diameter of 125 $\mu$m (denoted a 50/125 fiber) A single mode fiber, having a core diameter of 8 $\mu$m and a cladding diameter of 125 $\mu$m (a 8/125 may also be used. It is also possible to use a combination of one single mode fiber and one multimode fiber. For single mode fibers, the preferred core diameter is dependent on the wavelength of light to be used.

The distal end 21 of tube 24 is preferably closed by a cap 26, or the like, to prevent the intrusion of blood into the probe which might form undesirable clots.

An opening 28 is initially formed in a sidewall of the tube 24. Terminal ends 17, 19 of the optic fibers 16, 18, respectively, are located within the tube 24 adjacent opening 28.

A plug 30 composed of reflective material is disposed within the tube 24 between the terminal ends 17, 19 of the optic fibers 16, 18, respectively, and the distal end cap 26 of the tube 24. The plug 30 may be composed of any suitable reflective material, such as copper, stainless steel, silver, mirrored glass, or the like. Presently a portion of stainless steel wire having a diameter of 0.2 mm has been employed.

One end of the plug 30 nearest the terminal ends 17, 19 is ground and polished to form a finished reflective surface 32 that is oriented at an angle with respect to the longitudinal fiber axes of the fibers 16, 18. It is presently contemplated that the preferred angle of the reflective surface be within the range of about 25–35° with respect to the longitudinal fiber axes of the fibers 16, 18, wit h an angle of about 30° being preferred.

Once the fibers and the reflective surface are appropriately aligned, the cavity within the opening 28 surrounding the optic fibers 16, 18 and the plug 30 is filled with an optical cement 34. The optical cement may include any suitable optically transparent material having an initial liquid phase and which hardens after being poured into the cavity, such as clear polymeric materials which harden upon exposure to certain radiation. When set, the optical cement 34 locks the fibers and the reflective surface 32 together into an integral unit. The cement 34 also provides a smooth surface over the opening that is flush with the outer peripheral surface of tube 24. To this end, it is necessary that the optical cement, forming an optical window 35 when finished, be polished smooth to minimize turbulence caused by the surface and to prevent blood clots from forming in voids and other irregularities in the cement. The preferred optical cement is "Norland™ optical Adhesive 61". It should be understood, however, that other optical quality cements can also be employed.

In operation, with the catheter inserted into the blood vessel of a patient, a transmission, or incident, beam of light from a laser, preferably, a laser diode, such as, for example, the 7350 Series Diffraction Limited Laser Diode, operating in the wavelength range of 670–680 nm, produced by SDL, Incorporated of San Jose, Calif., U.S.A., or an HeNe laser, exits the terminal end 17 of the optical fiber 16, here designated as the transmitting, or transmission, fiber. The wavelength of the light may be any wavelength within the scattering spectrum of blood, which ranges from 450–850 nm. Wavelengths within the red portion of the spectrum, 600–720 nm, are most preferred because they provide the most scattering within blood.

Figure 6:
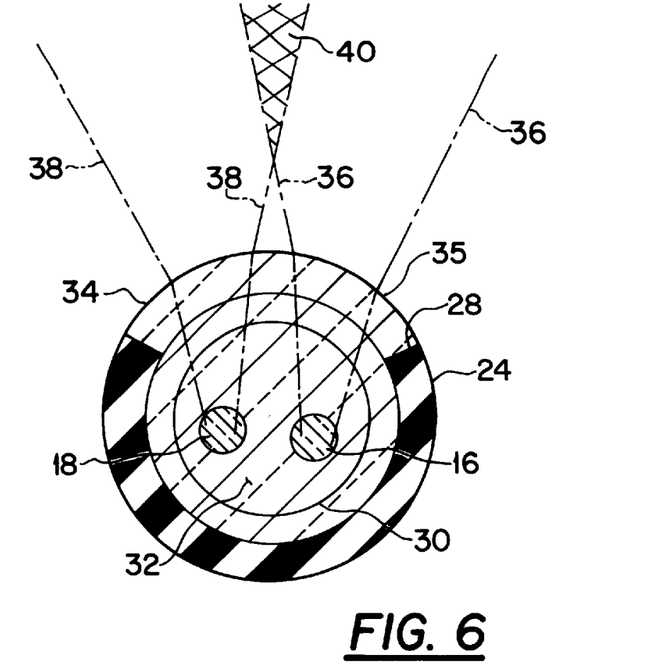
FIG. 6 is a cross-sectional view of the velocity sensor of FIG. 3 along the line "VI—VI"
Figure 7:
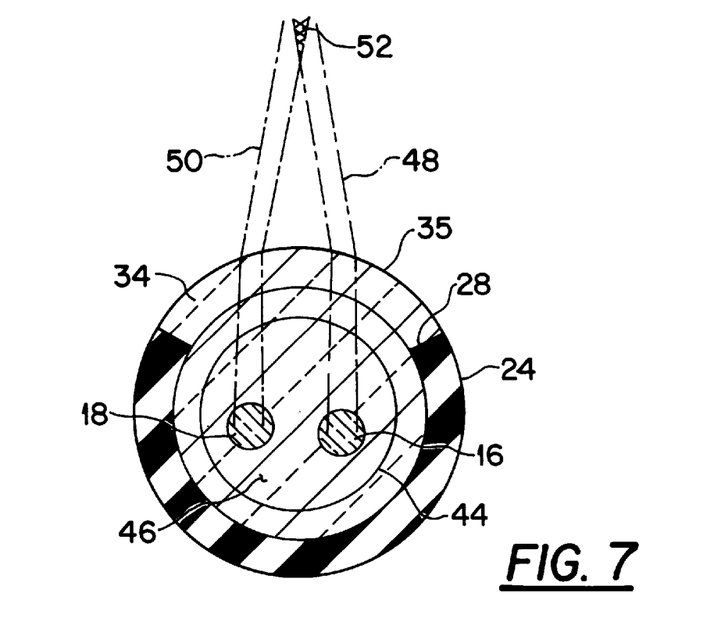
FIG. 7 is a cross-sectional view of the velocity sensor of FIG. 5 along the line "VI—VI" in FIG. 3.

The incident beam reflects off the reflecting surface 32 in a direction having a component normal to the fiber axes out of the optical window 35 formed over the opening 28 in the tube 24 (see FIG. 6). The light within the incident beam is reflected into a measurement, or probe, volume of fluid flow outside of and alongside the tube 24 in the region near the optical window 35. The reflected light is scattered by particles flowing within the measurement volume. A portion of the light is also scattered back (the backscatter) through the optical window 35 where it is reflected by the reflecting surface 32 into the terminal end 19 of the optical fiber 18, here designated as the receiving fiber. The light received by the receiving fiber 18 is known as the backscatter signal. The velocity of the fluid flow in the probe volume is determined in a known manner by analyzing the Doppler shift between the transmitted light and the backscatter signal.

As shown in FIG. 6, the reflected light emitted from the transmitting fiber 16 covers a diverging area denoted between lines 36, that can be considered as a transmitted acceptance cone. The receiving fiber 18 collects light from a diverging area , or acceptance cone or field of view, denoted between lines 38. The overlap of the transmitted acceptance cone 36 with the field of view 38, as shown by the cross-hatched area 40, represents the probe volume region wherein the incident beam and the backscatter transmission overlap. It is in this probe volume where fluid flow is measured.

The design parameters and the preferred values of those parameters will now be described.

Depending on the angle of the reflective surface, the probe volume maybe projected out of the optical opening normal to the fluid flow (i.e., normal to the fiber axes) or forwardly or rearwardly with respect to the fiber tips. To obtain the largest Doppler shift, however, it is preferred that the probe volume be projected as far forwardly or rearwardly as possible. If the probe volume is projected normally to the fiber axes, there is no Doppler shift and the flow velocity cannot be ascertained.

In addition, the height of the probe volume above the wall of the catheter 24 (i.e., the distance the probe volume 40 in FIG. 6 is spaced radially from the optic window 35) is also critical. The probe volume must be a sufficient distance, or at a sufficient projection height, from the catheter so that the probe volume is out of the boundary layer of the flow along the sidewall of catheter 24. On the other hand, if the probe volume is too far from the catheter sidewall, the laser transmission light cannot sufficiently penetrate the opaque blood. The projection height of the probe volume, thus, depends on a number of factors, including the index of refraction of the optical cement and the angle of the reflective surface. The greater the reflective surface angle, the higher the projection height. Projection height also depends on the position of the reflective surface with respect to the fiber tips. The closer the reflective surface is to the fiber tips, the higher the projection height. Finally, the projection height depends on the separation between the two fibers. The greater the separation, the greater the projection height.

To ensure that the acceptance cones of the transmission fiber and the receiving fiber are correctly projected out of the catheter and window 35, the two cones should intersect beyond the reflective surface. In other words, the two cones, between lines 36 and 38, respectively, cannot overlap until they are projected into the flow as shown in FIG. 6. To avoid overlap of the acceptance cones prior to their exiting optical window 35, the fiber core centers should be spaced at least 135 μm apart.

In addition, the reflective surface cannot be too far from the fiber tips. The beam angle of the transmission light depends on the index of refraction of the optical cement. Using the preferred optical cement, Norland™ Optical Adhesive 61, which has an index of refraction of 1.5562, the acceptance cones of two 50/125 multimode fibers, whose cores as separated by 135 μm, will intersect each other at a distance of 290 μm from the fiber tips. Therefore, the intersection of the fiber axes with the reflective surface must be within 290 Am of the fiber tips.

Although it is preferred that the probe volume 40 be projected as far forwardly or rearwardly along the catheter 24 as possible, the angle of the reflective surface cannot be so great or so small that the reflected transmission light does not leave the optical window due to total internal reflection. To avoid total internal reflection, the angle of the reflective surface must be between 25–65° from the fiber axes, but not, preferably, exactly 45°. Where the angle is progressing greater than 45°, the probe volume will be progressively projected rearwardly; as the angle becomes less than 450° the probe volume will be progressively projected forwardly. At a 45° reflective angle, the probe volume is projected normal to the fiber axes.

A forwardly projected probe volume is preferred. A normally projected probe volume would not capture sufficient Doppler shift, as noted above. While a rearwardly projected probe volume may be blocked by the fibers themselves, this could be avoided by moving the fibers a way from the reflective surface. This can, however, result in the acceptance cones of the fibers overlapping before reaching the reflective surface.

As noted previously, the angle of the reflective surface is preferably within the range of 25–35°, with 30° being preferred. If the angle is less than 25° total internal reflection will result. If the angle is greater than 35° the projection height will be too high.

The optical opening must be large enough so that the acceptance cones of the fibers are not blocked by the tube wall. For a sensor having 50/125 multimode fibers with a 135 μm separation between the fiber cores, an optical cement having an index of refraction of 1.5562, and a reflective surface with an angle of 30°, the optical opening must have an axial length of at least 600 μm measured axially from the fiber tips 17, 19 and a circumferential width of at least 530 μm that is centered between the optical fibers.

The plug 30 must have a sufficient diameter such that the acceptance cones of the fibers are entirely captured by the reflective surface. The diameter of the catheter primarily preferred herein is 1.2 mm. For a 1.2 mm diameter sensor having 50/125 multimode fibers with 135 μm separation therebetween, an optical cement having an index of refraction of 1.5562, a reflective surface at an angle of 30°, and with the fiber axes intersecting the reflective surface at a distance of 108.25 μm from the fiber tips, the outer diameter of the plug must be at least 204 μm.

For a sensor employing two 8/125 single mode fibers, the design parameters are summarized below:

| | |
|---|---|
| Refractive index of optical cement | 1.5562 |
| Recommended reflective angle | 27° |
| Minimum plug diameter | 150 μm |
| Minimum optical opening length for a 1.2 mm diameter sensor. | 400 μm |

It must be noted that the above preferred parameters have been developed for prototype sensors having flat reflective surface and normally positioned fiber tips. Any or all of the parameter values may differ in a preferred commercial embodiment from those cited above. In addition, it is important to understand that all of the parameters are directly interdependent and that variation of any one of the preferred values would necessarily change the remaining values.

In manufacturing the sensor of the present invention, the fibers are inserted into the tube with the plug on which the reflective surface is polished. Incident light transmitted through the transmission fiber and a received light signal are both monitored. The relative orientation of the fibers with respect to the protective surface is adjusted until the signal to noise ratio is maximized. The optical cement is then added to fix the relative positions of the fibers and the reflective surface.

The sensor of the present invention has been described thus far as having a single optical opening and window and a single reflective surface whereby the single window and reflective surface are associated with both fibers and each, respectively, transmits and reflects both the incidence signal and the backscatter signal. The sensor of the present invention could, however, include two or more reflective surfaces axially disposed with respect to associated fiber tips in a corresponding number of optical openings having associated optical windows. In this embodiment, it is contemplated that the incidence beam, emitted from a transmitting fiber, is reflected by its associated reflective surface out its associated optical window. Similarly, the backscatter signal passes through an optical window and is reflected by a reflective surface associated with a receiving fiber.

The sensor of the present invention has also be described as having a single transmitting a fiber and a single receiving fiber. It is presently contemplated, however, that the sensor of the present invention could include two or more transmitting fibers and/or two or more receiving fibers, at least one optic transmitting path and at least one optic receiving path being required.

It is desirable that the Doppler spectrum be as narrow as possible and that the signal to noise ratio be as large as possible. To maximize the signal to noise ratio from the sensor, and to minimize the width of the Doppler spectrum, it is desirable that the probe volume be as small as possible and that the transmission beam be as concentrated as possible. To that end, a sensor with the capability to focus the transmission signal and to focus the field of view of the receiving fiber would provide significant advantages over sensors without such capabilities.

Figure 5:
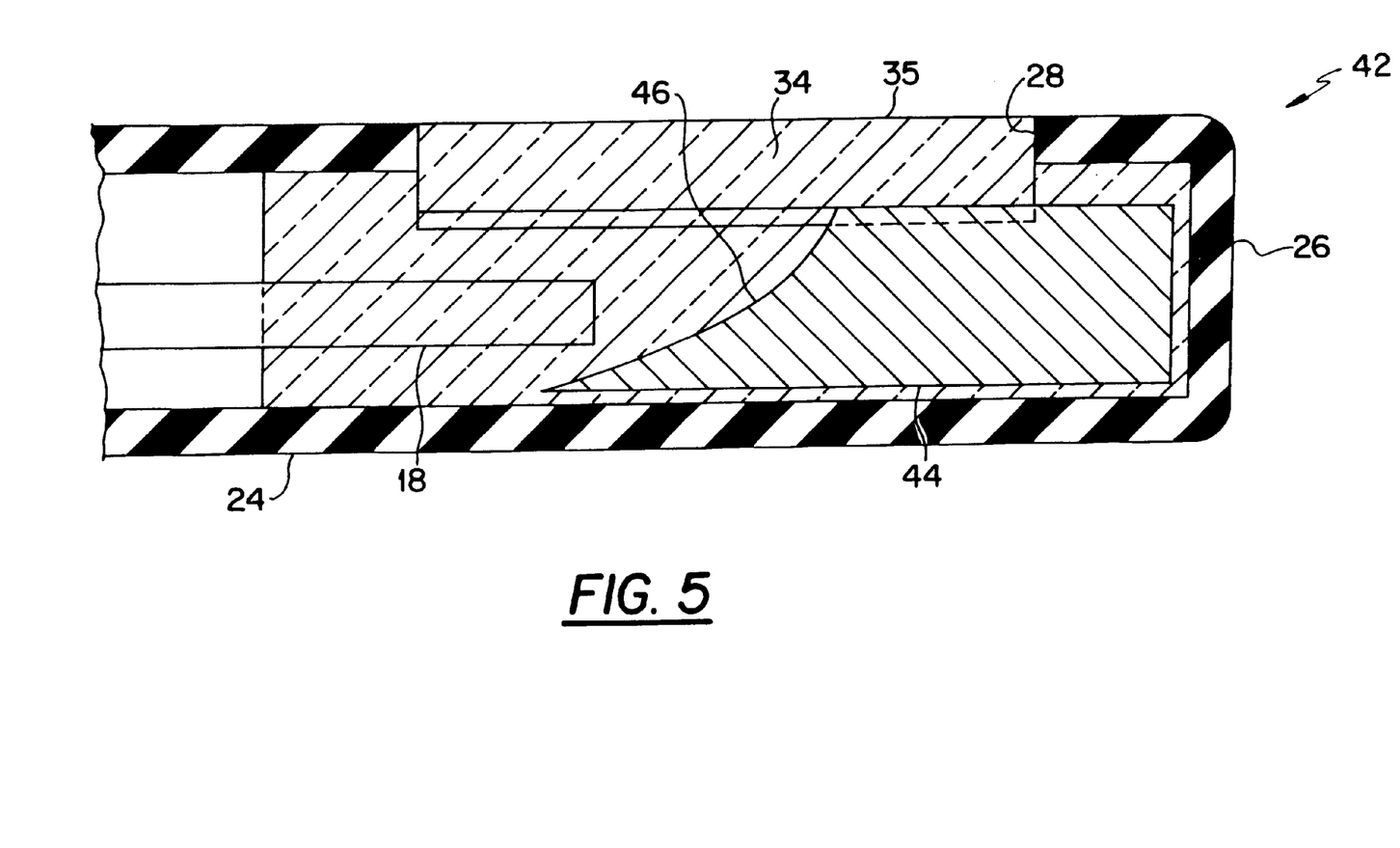
FIG. 5 is a cross-sectional view of a second embodiment of the velocity sensor in the direction "IV—IV" in FIG. 3.

An alternate embodiment of the fiber optic catheter of the present invention, which includes such focusing capability, is shown in FIGS. 5 and 7–9. The velocity sensor 42 of the catheter of the alternate embodiment shown in FIG. 5 is, in most respects, identical to the velocity sensor 14 of the first embodiment. The reflective surface 46 of the plug 44 is not, however, ground flat as in the first embodiment, but is ground with a concave shape as shown schematically in FIG. 5. As demonstrated in FIG. 7, the concave surface helps focus the incident beam 48 from the transmission fiber 16 to a smaller region above the surface of the sensor. Furthermore, by virtue of the concave reflective surface 46, the region from which light is collected by the receiving fiber 18, indicated between lines 50, is also focused so as to be narrower than without such focusing. This results in a narrower probe volume which results in a stronger signal to noise ratio and a narrower Doppler spectrum.

The index of refraction of the optical cement presently used is 1.5562. The index of refraction of the fiber core typically ranges from about 1.4–1.5. Accordingly, the acceptance cone of the transmission beam is enlarged upon being emitted from the fiber tip into the optical cement. This results in an undesired enlargement of the probe volume and a decrease in the light intensity. If the index of refraction of the optical cement were less than the index of refraction of the fiber core, however, the acceptance cone would shrink, resulting in built-in focusing effect.

The shape of the reflective surface can itself be modified to focus the transmission signal and the field of view of the receiving fiber. Similarly, the tips of the fibers may be shaped so as to produce such a focusing effect.

Figure 8A:
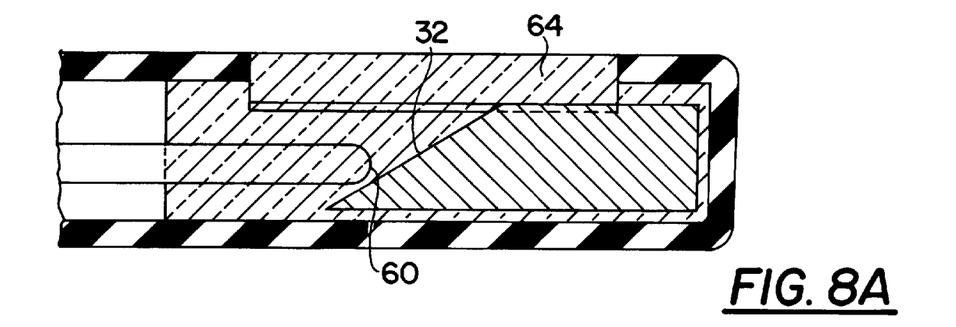
FIG. 8A is a cross sectional view of a velocity sensor depicting a third embodiment thereof.
Figure 8B:
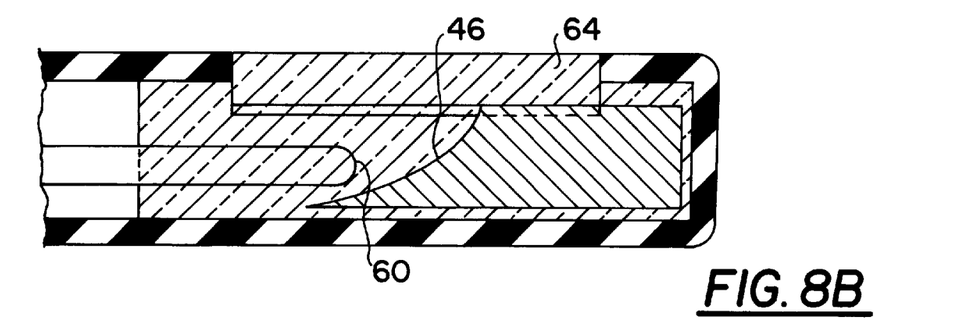
FIG. 8B is a cross sectional view of a velocity sensor depicting a fourth embodiment thereof.
Figure 9A:
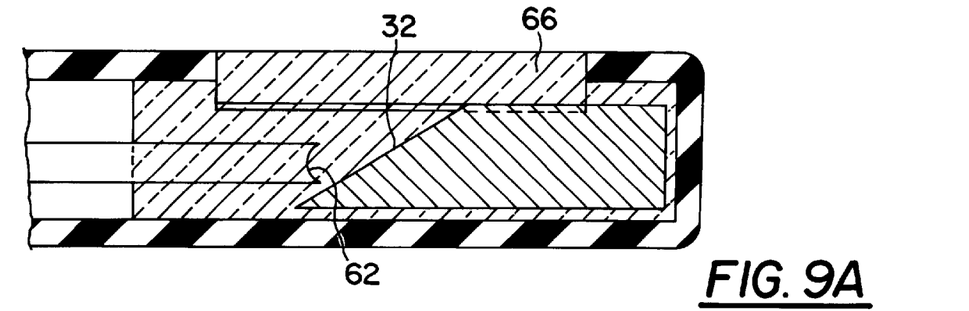
FIG. 9A is a cross sectional view of a velocity sensor depicting a fifth embodiment thereof.
Figure 9B:
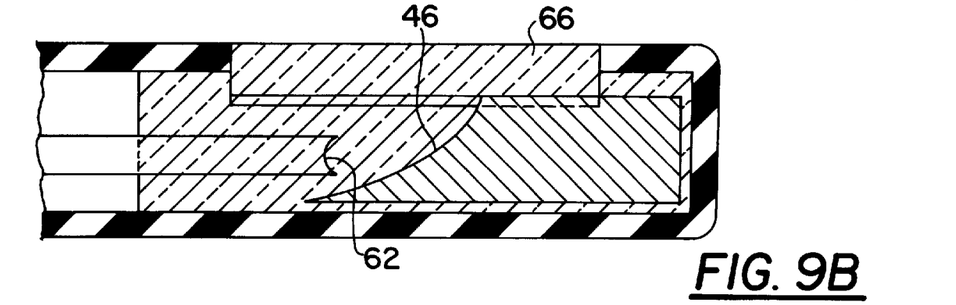
FIG. 9B is a cross sectional view of a velocity sensor depicting a sixth embodiment thereof.

Further embodiments of the sensor of the present invention are shown in FIGS. 8 and 9. The sensor of FIG. 9A, has fiber tips 60 that are convex in shape. Where the index of refraction of the optical cement 64 is less than the index of refraction of the fiber core, the convex fiber tips 60 of the sensor of FIG. 8A will result in a more focused probe volume and thus a stronger signal to noise ratio and narrower Doppler spectrum. Conversely, where the index of refraction of the optical cement 64 is greater than the index of refraction of the fiber core, the convex fiber tips 60 of the sensor of FIG. 8A will result in a less focused probe volume.

The sensor of FIG. 8A has a flat reflective surface 32. The sensor of FIG. 8B, has fiber tips 60 that are convex combined with a concave reflective surface 46 resulting in even more focusing of the probe volume.

The sensor of FIG. 9A has fiber tips 62 that are concave. Where the index of refraction of the optical cement 66 is greater than the index of refraction of the fiber core, the concave fiber tips 62 of the sensor of FIG. 9A will result in a more focused probe volume and thus a stronger signal to noise ratio and narrower Doppler spectrum. Conversely, where the index of refraction of the optical cement 66 is less than the index of refraction of the fiber core, the concave fiber tips 62 of sensor of FIG. 9A will result in a less focused probe volume.

The sensor of FIG. 9A has a flat reflective surface 32. The sensor of FIG. 9B, has fiber tips 62 that are concave combined with a concave reflective surface 46 resulting in even more focusing of the probe volume.

Figure 10:
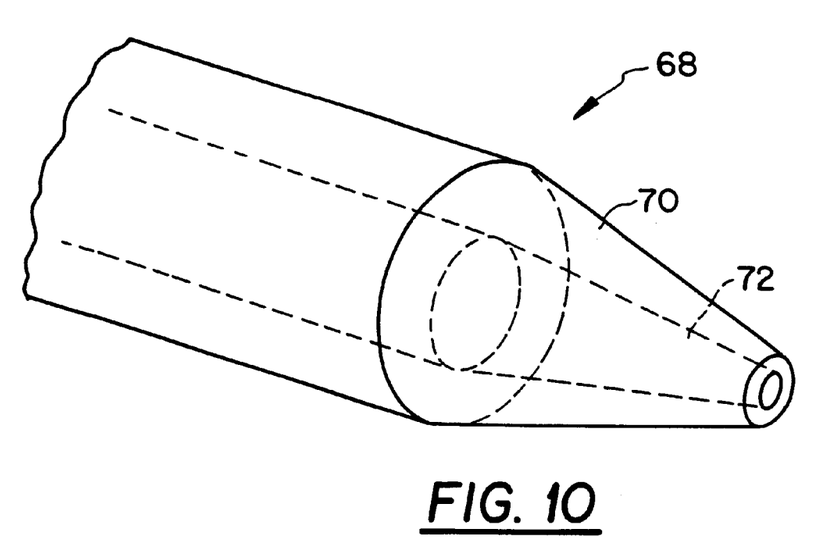
FIG. 10 is partial perspective view of an optic fiber having a conically shaped distal tip for focusing light emitted therefrom.
Figure 11:
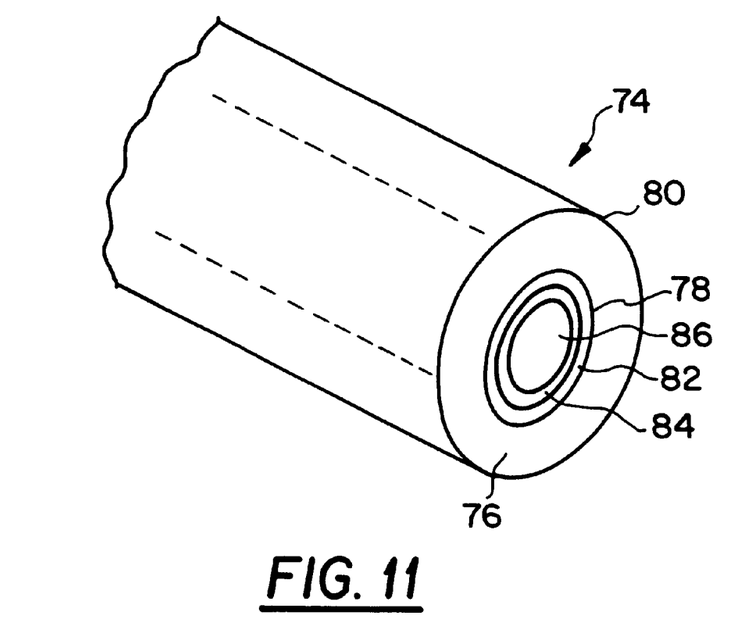
FIG. 11 is a partial perspective view of an optic fiber having a Fresnel zone plate formed on the distal tip thereof for focusing light emitted therefrom.

Further fiber tip variations for focusing the probe volume are shown in FIGS. 10–11.

In FIG. 10, fiber 68 includes a cladding 70 and core 72, both of which are formed in a cone at the distal end of fiber 68. Theoretically, the conical shape of the fiber tip will help focus the beam in front of the 9A fiber tip.

In FIG. 11, fiber 74 has a cladding 76, core 78, and distal tip 80. The core 78 at tip 80 is formed as a Fresnel zone plate, a series of concentric rings 82, 84, 86 being formed on tip 80. Light passing through the rings will be diffracted in a known manner, giving an intensity maximum at a point in front of the fiber. The distance from the fiber tips at which the light focuses depends on the spacing between adjacent rings and is dependent on the refractive index of the optical cement used for the optical window.

In analyzing the signals received by the receiving fiber of the two-fiber velocity sensor, the backscatter signal is compared to the incident signal in a known manner so as to determine the Doppler shift of the backscatter signal. As is well known in the art, the flow velocity of fluid, such as blood, is directly proportional to Doppler shift frequency. The velocity may be represented mathematically by the expression:

$$V = K \cdot f_D$$

where,
V=Blood Flow Velocity;
K=Doppler shift constant to be determined in a known manner; and
$f_D$=the Doppler shift frequency, to also be determined in a known manner.

The Doppler shift constant K is calculated by the following equation:

$$K = -\frac{2n}{\lambda}\cos\theta$$

where,
n=index of refraction of blood≈1.33;
θ=obtuse angle between direction of flow and the bisection of the transmission cone projected from the optical window; and
λ=wavelength the light.

While the invention has been described in connection with what are presently considered to be the most practical and preferred embodiments, it is to be understood that the invention is not to be limited to the disclosed embodiments, but, on the contrary, it is intended to cover various modifications and equivalent arrangements included within the spirit and scope of the appended claims.

For example, while the present invention has been describe predominantly in terms of its application for measuring volume flow rate in arteries, the present invention could, as well, be used in other applications in which a fluid is flowing through a conduit-like vessel.

It is to be understood, therefore, that variations in the particular parameters used in defining the improved fiber-optic probe can be made without departing from the novel aspects of this invention as defined in the claims.

What is claimed is:

1. An apparatus for continuously monitoring the volume flow rate of a fluid flowing through a vessel based on the relationship, Q=V×A, where Q is the volume flow rate, V is the velocity of the fluid flowing through the vessel, and A is the cross sectional area of the vessel proximate a location in the vessel where the flow velocity is measured, said apparatus comprising:

a cross-sectional area sensor for deriving the cross-sectional area of the vessel based on an electrical impedance within the vessel, said cross-sectional area sensor comprising an impedance measuring instrument constructed and arranged to continuously ascertain the electrical impedance of the vessel, the derived cross-sectional area being directly proportional to the resistivity, ρ, of the fluid flowing in the vessel and inversely proportional to the resistance, R, of the vessel;

a velocity sensor for measuring the velocity of the fluid flowing in the vessel; and a temperature sensor for continuously measuring the temperature of the fluid flowing in the vessel so as to allow continuous compensation in the cross-sectional area derivation for variations in the resistivity $\rho$ with temperature.

2. The apparatus of claim 1 wherein said temperature sensor comprises a thermistor.

3. The apparatus of claim 1 wherein said velocity sensor comprises:
 a flexible tube having an optical opening formed in a sidewall thereof;
 an optical fiber disposed within said tube, said optical fiber having a longitudinal fiber axis and a terminal end disposed proximate said optical opening; and
 a reflective surface disposed within said tube adjacent said terminal end of said optical fiber, said reflective surface being oriented such that light emitted from said terminal end of said optical fiber is reflected by said reflective surface in a direction having a component normal to the fiber axis through said optical opening into a measurement volume of the flow located outside and alongside said sensor.

4. The apparatus of claim 3 wherein said optical fiber includes an end face at said terminal end, said end face having a plurality of concentric Fresnel rings formed thereon to focus light passing through said Fresnel rings in front of said end face.

5. The apparatus of claim 3 wherein said terminal end is formed in a generally conical shape to focus light passing through said optical fiber in front of said terminal end.

6. The apparatus of claim 1 wherein said impedance measuring instrument of said cross-sectional area sensor comprises:
 a pair of signal-emitting electrodes for injecting a known electrical signal into the vessel in which said instrument is disposed;
 a first pair of measurement electrodes across which a voltage can be measured; and
 a second pair of measurement electrodes across which a voltage can be measured,
  wherein said signal-emitting electrodes inject the known signal into the vessel, a first voltage is measured across said first pair of measurement electrodes, and a second voltage is measured across said second pair of measurement electrodes, and the impedance of the vessel, from which the cross-sectional area can be derived, is determined from the known signal and the difference between the first and second voltages.

7. A method for continuously monitoring the volume flow rate of a fluid flowing through a vessel based on the relationship, $Q = V \times A$, where Q is the volume flow rate, V is the velocity of the fluid flowing through the vessel, and A is the cross sectional area of the vessel proximate a location in the vessel where the flow velocity is measured, said method comprising:
 ascertaining the electrical impedance of the vessel and deriving the cross-sectional area of the vessel based on the electrical impedance within the vessel, wherein the derived cross-sectional area is directly proportional to the resistivity, $\rho$, of the fluid flowing in the vessel and inversely proportional to the resistance, R, of the vessel;
 measuring the velocity of the fluid flowing in the vessel; and measuring the temperature of the fluid flowing in the vessel and compensating in the cross-sectional area derivation for variations in the resistivity $\rho$ with temperature based upon the measured temperature.

8. A velocity sensor for remote fluid flow measurements, said sensor comprising:
 a flexible tube having an optical opening formed in a sidewall thereof;
 an optical fiber disposed within said tube, said optical fiber having a longitudinal fiber axis, a terminal end disposed proximate said optical opening, and an end face at said terminal end, said end face having a plurality of concentric Fresnel rings formed thereon to focus light passing through said Fresnel rings in front of said end face; and
 a reflective surface disposed within said tube adjacent said terminal end of said optical fiber,
 said reflective surface being oriented such that the focused light emitted from said terminal end of said optical fiber is reflected by said reflective surface in a direction having a component normal to the fiber axis through said optical opening into a measurement volume of the flow located outside and alongside said sensor.

9. The sensor of claim 1 further comprising:
 a second optical fiber disposed within said tube, said second optical fiber having a longitudinal fiber axis, a terminal end disposed adjacent said reflective surface, and an end face at said terminal end, said end face of said second optical fiber having a plurality of concentric Fresnel rings formed thereon to focus light passing through said Fresnel rings into said end face of said second optical fiber to define, along with said reflective surface, a focused field of view of the second optical fiber into the measurement volume,
 wherein said reflective surface is oriented such that a portion of the focused light from said first mentioned optical fiber which is reflected into the measurement volume of the flow and scattered within the measurement volume is within the focused field of view of said second optical fiber.

10. A velocity sensor for remote fluid flow measurements, said sensor comprising:
 a flexible tube having an optical opening formed in a sidewall thereof;
 an optical fiber disposed within said tube, said optical fiber having a longitudinal fiber axis and a terminal end disposed proximate said optical opening, said terminal end being formed in a generally conical shape to focus light passing through said optical fiber in front of said terminal end; and
 a reflective surface disposed within said tube adjacent said terminal end of said optical fiber,
 said reflective surface being oriented such that the focused light emitted from said terminal end of said optical fiber is reflected by said reflective surface in a direction having a component normal to the fiber axis through said optical opening into a measurement volume of the flow located outside and alongside said sensor.

11. The sensor of claim 10 wherein comprising:
 a second optical fiber disposed within said tube, said second optical fiber having a longitudinal fiber axis and a terminal end disposed adjacent said reflective surface, said terminal end of said second optical fiber being formed in a generally conical shape to focus light passing through said terminal end of said second optical fiber to define, along with said reflective surface, a focused field of view of the second optical fiber into the measurement volume, wherein said reflective surface is oriented such that a portion of the focused light from said first mentioned optical fiber which is reflected into the measurement volume of the flow and scattered within the measurement volume is within the focused field of view of said second optical fiber.

12. An instrument for ascertaining the impedance of a vessel in which said instrument is disposed, the cross-sectional area of the vessel being derivable from the ascertained impedance, said instrument comprising:

a pair of signal-emitting electrodes for injecting a known electrical signal into the vessel in which said instrument is disposed;

a first pair of measurement electrodes across which a voltage can be measured; and a second pair of measurement electrodes across which a voltage can be measured, wherein said signal-emitting electrodes inject the known signal into the vessel, a first voltage is measured across said first pair of measurement electrodes, and a second voltage is measured across said second pair of measurement electrodes, and the impedance of the vessel, from which the cross-sectional area can be derived, is determined from the known signal and the difference between the first and second voltages.

13. The instrument of claim 5 comprising six electrically-conducting rings longitudinally spaced along a catheter tube wherein two outermost rings of said six rings constitute said pair of signal emitting electrodes, two innermost rings constitute said first pair of measurement electrodes, and two intermediate rings, each being disposed between a one of the innermost rings and a one of the outermost rings, constitutes said second pair of measurement electrodes.

* * * * *